US00PP13493P3

(12) United States Plant Patent
Olesen et al.

(10) Patent No.: US PP13,493 P3
(45) Date of Patent: Jan. 21, 2003

(54) MINIATURE ROSE PLANT NAMED 'POULHI001'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 15 days.

(21) Appl. No.: 09/780,133

(22) Filed: Feb. 8, 2001

(65) Prior Publication Data

US 2002/0166150 P1 Nov. 7, 2002

(51) Int. Cl.[7] ..... A01H 5/00
(52) U.S. Cl. ..... Plt./118
(58) Field of Search ..... Plt./118

(56) References Cited

PUBLICATIONS

UPOV–ROM GTITM Computer Database, 2001/06, GTI Jouve Retrieval Software, citation for 'POULhi001'.*

* cited by examiner

*Primary Examiner*—Bruce R. Campell
*Assistant Examiner*—Susan B. McCormick

(57) ABSTRACT

A new miniature rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

Classification:
*Botanical.*—*Rosa hybrida* 'POULhi001'.
*Commercial.*—Miniature.

The present invention constitutes a new and distinct variety of miniature rose plant which originated from a controlled crossing between an 'unnamed seedling' and 'Rumba', both unpatented varieties. The two parents were crossed and the resulting seeds were planted in a controlled environment.

The new variety is named 'POULhi001'.

The new rose may be distinguished from its seed parent, an unnamed seedling, by the following combination of characteristics:

1. The seed parent is a floribunda rose whereas 'POULhi001' is a miniature rose.
2. The habit of the seed parent is much taller and wider than 'POULhi001'.

The new variety may be distinguished from its pollen parent, 'Rumba', an unpatented rose created by the same inventors, by the following combination of characteristics:

1. The pollen parent has bicolor flowers (red and yellow) whereas 'POULhi001' has yellow flowers.
2. The pollen parent is taller and is utilized commercially for cut flowers whereas 'POULhi001' is more compact and is suitable for commercial pot rose production.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;

5. Durable flowers and foliage which make a variety suitable for distribution in the floral industry.

This combination of qualities is not present in previously available commercial cultivars of this type and distinguish 'POULhi001' from all other varieties of which we are aware.

As part of their rose development program, L. Pernille Olesen and Mogens N. Olesen germinated the seeds from the aforementioned hybridization in winter 1996 and conducted evaluations on the resulting seedlings in a controlled environment in Fredensborg, Denmark.

'POULhi001' was selected by the inventors as a single plant from the progeny of the hybridization in spring 1997.

Asexual reproduction of 'POULhi001' by cuttings and traditional budding was first done by L. Pernille and Mogens N. Olesen in their nursery in Fredensborg, Denmark in June 1997. This initial and other subsequent propagations conducted in controlled environments have demonstrated that the characteristics of 'POULhi001' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULhi001'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULhi001', as observed in its growth in Burlington, Ontario, Canada. Color references are made using The Royal Horticultural Society (London, England) Colour Chart, 1995, except where common terms of color are used.

For a comparison, several physical characteristics of the rose variety 'POULmoon', a rose variety from the same inventors described and illustrated in U.S. Plant Pat. No. 11,673 and issued on Sep. 12, 2000 are compared to 'POULhi001' in Chart 1.

CHART 1

| | 'POULhi001' | 'POULmoon' |
|---|---|---|
| After opening, outer petal, upper surface | Yellow-Orange Group 15C | Yellow Group 4C |
| After opening, outer petal, lower surface | Yellow-Orange Group 15A | Yellow Group 4C |
| Petalage | 40–50 | 35–40 |

Parents: 'Unnamed seedling'×'Rumba'.

FLOWER AND FLOWER BUD

Blooming habit: Continuous.

Flower bud:

*Size.*—Upon opening, 20 mm in length from base of receptacle to end of bud. Diameter is 25 mm.

*Bud form.*—Short and globular.

*Bud color.*—As sepals unfold, Green-Yellow Group 1C with out guard petals having intonations of Red Group 51A. Yellow-Orange Group 20A at ¼ opening.

*Sepals.*—Green Group 137A. Strong foliaceous appendages on 3 of the 5 sepals. Surfaces of sepals moderately pubescent on sepals which do not have foliaceous appendages and very slightly pubescent on sepals with foliaceous appendages. Stipitate glands are present along the margins of the sepals. Sepals are 20 mm long and 10 mm wide.

*Receptacle.*—Surface: Smooth. Shape: Urn-shaped. Size: Small. 4–6 mm(h)×8–11 mm (w). Color: Yellow-Green Group 144C.

*Peduncle.*—Surface: Moderate number of stipitate glands. Length: 30–35 mm average length. Color: Yellow-Green Group 144A. Strength: Upright. Anthocyanin: None.

*Borne.*—Multiple buds per stem (1–3).

Flower bloom:

*Fragrance.*—Light, fruity scent.

*Duration.*—As a pot plant, flowers last from 7 to 10 days. As a cut flower, 4 to 5 days. The blooms have a duration on the plant of approximately 7 to 10 days.

*Size.*—Large for a 12–15 cm pot rose. Average flower diameter is 45–55 mm when open.

*Form.*—Shape of flower when viewed from the side: Upon opening, upper part: Flat. Upon opening, lower part: Flattened convex. Open flower, upper part: Flattened convex. Open flower, lower part: Concave.

*Petalage.*—Very double. Average range: 38–45 petals under normal conditions with 0–5 petaloids.

Color:

*Upon opening, petals.*—Outermost petals: Outer Side: Yellow Group 12C. Guard petals may exhibit intonations of Red Group 53A and Yellow-Green Group 144A–B. Inner Side: Yellow Group 13A. Innermost petals: Outer Side: Yellow Group 13B. Inner Side: Yellow-Orange Group 14B. Innermost petals occasionally exhibit intonations of Green-White Group 157C–D emanating from the basal point to the middle zone of the petal. Upon opening, basal petal spots: No distinctive coloration at petal base observed.

*After opening, petals.*—Outermost petals: Outer Side: Yellow-Orange Group 15C. Guard petals may exhibit intonations of Red Group 52A and Yellow-Green Group 144B–C. Inner Side: Yellow-Orange Group 15A. Innermost petals: Outer Side: Yellow-Orange Group 15C. Inner Side: Yellow-Orange Group 15B.

*After opening, basal petal spots.*—No distinctive coloration at petal base observed.

General tonality: On open flower, Yellow Group 13B. No change in the general tonality at the end of the $4^{th}$ day. Afterwards, general tonality is Yellow-Orange Group 13C.

Petals:

*Petal reflex.*—Moderate.

*Petal edge.*—Weakly undulated.

*Shape.*—Round to deltoid. Base is rounded.

*Size.*—20 mm wide and 18 to 20 mm long.

*Petaloids.*—Present. Quantity: 0–5.

*Thickness.*—Thin.

*Arrangement.*—Imbricated.

*Texture.*—Velvety.

Reproductive organs:

*Pollen.*—Color: Greyed-Orange Group 166B. Quantity: Very abundant.

*Anthers.*—Size: Medium. Color: Yellow Group 5C. Quantity: 35 to 40.

*Filaments.*—Color: Yellow-Orange Group 14A.

*Stigmas.*—Superior in location to anthers. Color: Yellow-Green Group 144D.

*Styles.*—Color: Yellow-Green Group 145D.

*Seed formation.*—Hips not observed on pot plants.

PLANT

Plant growth: Vigorous and compact. When grown as a 12–15 cm pot plant, the average height of the plant itself is 22–25 cm and the average width is 20–25 cm.

Stems:

*Color.*—Young wood: Green Group 143C. Older wood: Green Group 143B.

*Size.*—Length: 30 to 35 cm. Diameter: 5 to 7 mm.

*Prickles.*—Incidence: Few. Size: Average length: 3–5 mm. Color: Greyed-Orange Group 163A. Shape: Concave.

*Surface.*—Young wood: Smooth. Older wood: Smooth.

Plant foliage: Typical number of leaflets on normal leaves in middle of the stem: 5 leaflets.

*Typical leaf size.*—Medium. 85–100 mm (l)×65–85 mm (w).

*Quantity.*—Very abundant.

*Color.*—Upper leaf surface: Green Group 139A to Yellow-Green Group 147A. Lower leaf surface: Yellow-Green Group 147B. Juvenile foliage: Upper leaf surface: Green Group 137A. Lower leaf surface: Green Group 137C. Anthocyanin: On leaflet margins of juvenile foliage. Color: Greyed-Purple Group 184A.

Plant leaves and leaflets:

*Stipules.*—Size: 5–9 mm (l)×3–4 mm (w). Color: Yellow-Green Group 144B.

*Stipitate glands.*—On margins and underside of stipules. Anthocyanin: None.

*Petiole.*—Length: 20–30 mm. Diameter: 3 to 4 mm. Color: Yellow-Green Group 144C. Underneath: Smooth. Margins: Stipitate glands along margins on upper surface. Anthocyanin: On upper surface of mature and immature foliage. Color: Greyed-Red Group 181C.

*Rachis.*—Color: Yellow-Green Group 144C. Underneath: Small prickles where leaflets attach to rachis and a very limited number of stipitate glands. Margins: Moderate number of stipitate glands along upper margins. Anthocyanin: Along margins of mature and juvenile rachis. Color: Red-Purple Group 185A.

*Leaflet.*—Size: 35 mm (l)×25–30 mm (w). Edge: Serrated. Shape: Broadly ovate. Base is rounded, apex is acute. Other: Glossy and thin. Venation: Reticulate. Vein color is Yellow-Green Group 151A.

Disease resistance: Above average resistance to mildew, black spot, and Botrytis under normal growing conditions in Burlington, Canada.

Cold hardiness: The variety 'POULhi001' has been found to be resistant to damage from cold in USDA Zone 7.

We claim:

1. A new and distinct variety of rose plant of the miniature class, substantially as herein illustrated and described as a distinct and novel rose variety due to its abundant yellow flowers, vigorous growth, compact habit, suitability for production from softwood cuttings in pots, and durable flowers and foliage which make the variety suitable for distribution in the floral industry.

* * * * *

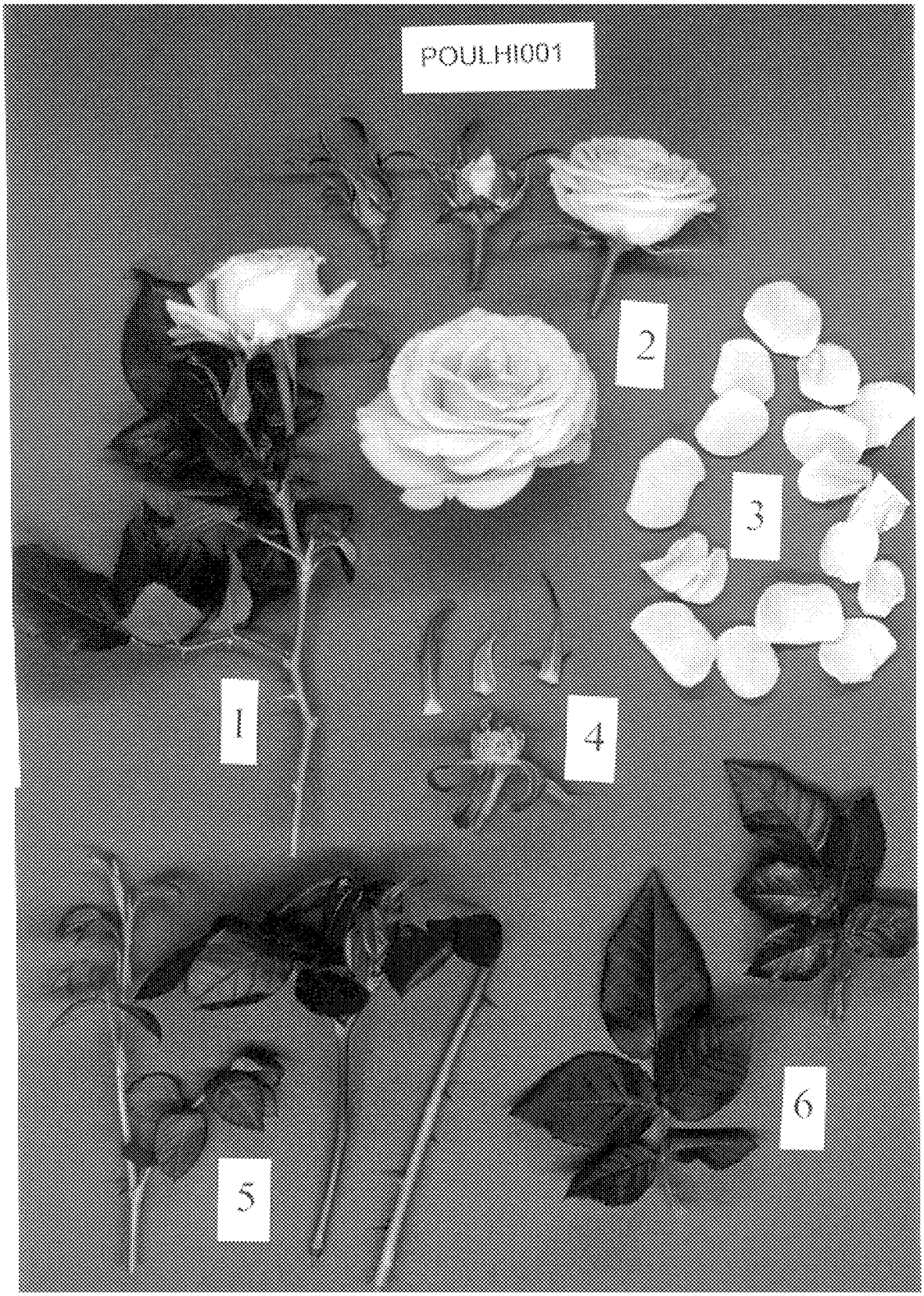
POULHI001
1
2
3
4
5
6